United States Patent [19]

Gauthier-Lafaye et al.

[11] 4,324,927

[45] Apr. 13, 1982

[54] PROCESS FOR THE HOMOLOGIZATION OF METHANOL

[75] Inventors: Jean Gauthier-Lafaye, Lyons; Robert Perron, Charly, both of France

[73] Assignee: Rhone-Poulenc Industries, Paris, France

[21] Appl. No.: 155,932

[22] Filed: Jun. 3, 1980

[30] Foreign Application Priority Data

Jun. 7, 1979 [FR] France .................................. 79 15079

[51] Int. Cl.³ ........................ C07C 29/32; C07C 29/36
[52] U.S. Cl. .................................................. 568/902
[58] Field of Search ........................................... 568/902

[56] References Cited

U.S. PATENT DOCUMENTS

| | | | |
|---|---|---|---|
| 3,285,948 | 11/1966 | Butter | 568/902 |
| 4,126,752 | 11/1978 | Novotny et al. | 568/902 |
| 4,133,966 | 1/1979 | Pretzer et al. | 568/902 |
| 4,171,461 | 10/1979 | Bartish | 568/902 |
| 4,233,466 | 11/1980 | Fiato | 568/902 |

FOREIGN PATENT DOCUMENTS

877598  5/1953  Fed. Rep. of Germany .
1323453  2/1963  France .
1341840  9/1963  France .

OTHER PUBLICATIONS

Wender et al., "Science", vol. 113, pp. 206 and 207, (1951).

*Primary Examiner*—Joseph E. Evans
*Attorney, Agent, or Firm*—Ronald A. Schapira

[57] ABSTRACT

A process for the homologization of methanol to produce ethanol, comprising carbonylating methanol in the simultaneous presence of hydrogen, cobalt, ruthenium, at least one ionic halide, and at least one alkyl halide, the molar ratio Ru/Co being at least about 2.

18 Claims, No Drawings

PROCESS FOR THE HOMOLOGIZATION OF METHANOL

BACKGROUND OF THE INVENTION

The present invention relates to an improved process for the preparation of ethanol by the hydrocarbonylation of methanol in the presence of a cobalt-based catalyst.

Ethanol, which is a very valuable industrial product, has conventionally been prepared by the fermentation of various natural substances or by the direct or indirect hydration of ethylene. Numerous processes of industrial synthesis have been developed which use charges of ethylene, this being a petroleum derivative. However, a growing need for processes for the synthesis of heavy chemical products starting from raw materials which do not originate from petroleum has been observed for some years. It is for this reason that it is possible to see an increasingly active interest in the synthesis of chemical products from synthesis gas, i.e., a mixture of carbon monoxide and hydrogen.

In this context, methanol, which can be produced by reacting carbon monoxide with hydrogen and which, in turn, can be reacted with synthesis gas in the presence of cobalt in order to form ethanol, has a very particular importance.

The reaction of methanol with synthesis gas in order to form ethanol, which reaction is still referred to as the homologisation of methanol, has formed and continues to form the subject of much research.

Thus, I. Wender et al. ("Science," Volume 113, page 206, 1951) have shown that methanol reacts with an equimolar mixture of carbon monoxide and hydrogen at 185° C., under a pressure of 360 atmospheres, in the presence of dicobalt octacarbonyl. Under these conditions, a mixture of various products containing ethanol is obtained with a mediocre selectivity. The advantage of this technique has remained purely academic, the hourly productivity of such a catalyst being absurdly low.

Other authors (compare French Pat. No. 1,323,453) have been able substantially to improve the productivity in respect to ethanol by carrying out this reaction at 400 bars and at about 200° C., in the simultaneous presence of cobalt acetate and iodine, the molar ratio $CO/H_2$ being equal to 0.5.

Subsequently, the same authors further increased this productivity considerably by carrying out the homologisation reaction under the conditions referred to above, with the addition of a very low proportion of a ruthenium halide to the catalyst system based on cobalt acetate and iodine (compare U.S. Pat. No. 3,285,948). In fact, the best results are obtained with about 0.05 to 0.12 gram atom of ruthenium per gram atom of cobalt and correspond to productivities of the order of 350 to 400 g. of ethanol per hour and per liter of reaction medium, and of the order of 200 g. of ethanol per hour and per gram of cobalt (compare Examples Nos. 4, 7, and 12 of the above-mentioned U.S. Patent).

Nevertheless, the possible industrial exploitation of such a process is jeopardized by the elevated pressure required to achieve acceptable hourly productivities.

It has now been found, totally unexpectedly, that it is possible to homologise methanol, under a total pressure of less than 400 bars, with an acceptable hourly productivity in respect to ethanol, in the presence of a cobalt-based catalyst.

It is, therefore, an object of the present invention to provide a novel process for the homologisation of methanol to produce ethanol in commerically practical yields.

It is also an object of the present invention to provide a process for producing ethanol from methanol by homologisation which employs practical pressures.

Other objects will be apparent to those skilled in the art from the present description.

GENERAL DESCRIPTION OF THE INVENTION

The present invention comprises a process for the hydrocarbonylation of methanol in the simultaneous presence of an effective amount of cobalt, at least one ionic halide, at least one alkyl halide, and at least 2 gram atoms of ruthenium per gram atom of cobalt.

The research which led to the present invention has shown, in a manner which is in itself remarkable, that the addition of an ionic halide and an alkyl halide to the catalyst system based on cobalt and ruthenium, the ratio Ru/Co being more than 2, substantially increases the activity of such a system, and this makes it possible to carry out the homologisation of methanol under a total pressure of the order of about 250 bars while at the same time obtaining a satisfactory hourly productivity.

The process according to the invention requires the use of at least one ionic halide. The term "ionic halide" is understood to mean those inorganic or organic chlorides, bromides, or, preferably, iodides. The cations of these halides are preferably chosen from among alkali metal cations, alkaline earth metal cations, and the quaternary ammonium or phosphonium cations represented by the formulae I to III, below:

in which A represents a nitrogen or phosphorus atom and $R_1$, $R_2$, $R_3$, and $R_4$, which may be identical or different, represent hydrogen, or preferably, organic radicals of which the free valency is carried by a carbon atom; optionally, any two of these radicals may together form a single divalent radical.

More specifically, $R_1$, $R_2$, $R_3$, and $R_4$, may represent linear or branched alkyl radicals or monocyclic cycloalkyl, aralkyl (for example, benzyl), or aryl radicals, which have, at most, about 16 carbon atoms and which may be substituted by about 1 to 3 alkyl radicals having from about 1 to 4 carbon atoms; optionally, two of the radicals $R_1$ to $R_4$ may together form a single, divalent, alkylene, or alkenylene radical containing about 3 to 6 carbon atoms (for example, a tetramethylene or hexamethylene radical) and, optionally, about 1 or 2 ethylenic double bonds, it being possible for the said radical to carry about 1 to 3 alkyl substituents having from about 1 to 4 carbon atoms.

in which $R_5$, $R_6$, $R_7$, and $R_8$, which are identical or different, represent alkyl radicals having from about 1 to 4 carbon atoms, it further being possible for one of the radicals $R_7$ or $R_8$ to represent hydrogen, and it being possible, optionally, for $R_7$ and $R_8$ together to form a single, divalent alkylene radical containing from about 3 to 6 carbon atoms, for example, a tetramethylene or hexamethylene radical; $R_6$ and $R_7$ or $R_8$ may together form a single, divalent, alkylene or alkenylene radical containing 4 carbon atoms and, optionally, about 1 or 2 ethylenic double bonds, the nitrogen atom then being included in a heterocyclic ring in order to form, for example, a pyridinium cation.

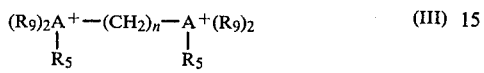   (III)

in which $R_5$ and $A^+$ have the meaning given above, $R_9$, which may be identical to $R_5$, represents an alkyl radical having from about 1 to 4 carbon atoms, or a phenyl radical, and n is an integer between about 1 and 10 ($1 \leq n \leq 10$) and preferably between about 1 and 6 ($1 \leq n \leq 6$).

Examples which may be mentioned of quaternary ammonium halides which are suitable for carrying out the present process are tetramethylammonium, triethylmethylammonium, tributylmethylammonium, trimethyl-(n-propyl)-ammonium, tetraethylammonium, tetrabutylammonium, dodecyltrimethylammonium, benzyltrimethylammonium, benzyldimethylpropylammonium, benzyldimethyloctylammonium, dimethyldiphenylammonium, methyltriphenylammonium, N,N-dimethyltrimethyleneammonium, N,N-diethyl-trimethyleneammonium, N,N-dimethyltetramethyleneammonium, N,N-diethyl-tetramethyleneammonium, N-methylpyridinium, N-ethylpyridinium, and N-methylpicolinium chlorides, bromides, and, more particularly, iodides.

Examples which may be mentioned of quaternary phosphonium halides which are also suitable for carrying out the present process are tetramethylphosphonium, ethyltrimethylphosphonium, trimethylpenytlphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)-phosphonium, methyl-tri-(n-propyl)-phosphonium, methyl-tri-(n-butyl)-phosphonium, methyl-tris (2-methylpropyl)-phosphonium, methyltricyclohexylphosphonium, methyltriphenylphosphonium, methyltribenzylphosphonium, methyl-tris-(4-methylphenyl)-phosphonium, methyltrixylylphosphonium, diethylmethylphenylphosphonium, dibenzylmethylphenylphosphonium, ethyltriphenylphosphonium, tetraethylphosphonium, ethyl-tri-(n-propyl)-phosphonium, triethylpentylphosphonium, ethyltriphenylphosphonium, n-butyl-tri-(n-propyl)-phosphonium, butyltriphenylphosphonium, benzyltriphenylphosphonium, ($\beta$-phenylethyl)-dimethylphenylphosphonium, tetraphenylphosphonium, and triphenyl-(4-methylphenyl)-phosphonium chlorides, bromides, and more particularly, iodides.

The specific quaternary ammonium or phosphonium cation employed is not of fundamental importance within the scope of the process of the present invention. The choice from among these compounds is governed more by practical considerations, such as the solubility in the reaction medium, the availability and the convenience of use. In this respect, the quaternary ammonium or phosphonium halides represented either by the formula (I) in which any one of the radicals $R_1$ to $R_4$ is chosen from among linear alkyl radicals having from about 1 to 4 carbon atoms, or by the formulae (II) or (III) in which $R_5$ (or $R_6$) is also an alkyl radical having from about 1 to 4 carbon atoms, are particularly suitable.

Moreover, the preferred ammonium halides are those in which the cations correspond to the formula (I) in which all the radicals $R_1$ to $R_4$ are chosen from among linear alkyl radicals which have from about 1 to 4 carbon atoms and at least three of which are identical.

Likewise, the preferred quaternary phosphonium halides are those in which the cations correspond to the formula (I) in which any one of the radicals $R_1$ to $R_4$ represents a linear alkyl radical having from about 1 to 4 carbon atoms, the other three radicals being identical and being chosen from among phenyl, tolyl, or xylyl radicals.

The quaternary phosphonium iodides, and more particularly, those in which the cations correspond to the above formula (I) in which one of the radicals $R_1$ to $R_4$ is an alkyl radical having from about 1 to 4 carbon atoms, the other three radicals being identical and being chosen from among phenyl, tolyl, or xylyl radicals, constitute a class of ionic halides which are particularly convenient for practicing the present invention.

A preferred embodiment of the present invention comprises the use of alkali-metal or alkaline earth metal iodides, such as: LiI, NaI, KI, CsI, CaI$_2$ and MgI$_2$. Preferably, one or more alkali-metal iodides are used; even more advantageously, NaI or KI is used.

According to the present invention, the molar ratio $X^-/Co$, $X^-$ being the halide ion originating from the ionic halide, should be equal to at least about 5. It is not desirable for this ratio to exceed a value of about 200. Very satisfactory results are obtained for a ratio $X^-/Co$ of the order of about 10 to 100.

The process of the invention also requires the use of at least one alkyl halide, that is to say, a compound of the formula RX, in which X represents a chlorine or bromide atom or, preferably, an iodine atom, and R is an alkyl radical having a maximum of about 16 carbon atoms. Of course, the methyl halides which can initially be introduced into the reaction medium are capable of being formed in situ from halogen derivatives, such as Cl$_2$, Br$_2$, I$_2$, HCl, HBr, HI, CoBr$_2$, CoI$_2$, RuCl$_3$, and RuI$_3$, with methanol (starting material). In other words, all or part of the methyl halide necessary for carrying out the present process can be formed from the precursors defined above.

It will also be seen that, if the halogen derivative is chosen from among the cobalt compounds or the ruthenium compounds, it can be considered not only as a precursor of the methyl halide, but also a precursor of the metal catalyst (or catalysts). In this particular case, it proves preferable also to introduce, initially, an alkyl halide and/or a precursor of the methyl halide, which is different from the metal halides in question.

The invention envisages, in particular, the use of lower alkyl chlorides, bromides and iodides having from about 1 to 4 carbon atoms in the molecule, such as methyl bromide and iodide, ethyl bromide and iodide, and propyl bromide and iodide. Methyl iodide and/or one of its potential sources chosen from among iodine, hydriodic acid, cobalt iodide, and ruthenium iodide, is preferably used.

According to the present invention, the molar ratio X/Co, X being the halogen originating from the alkyl halide, is equal to at least about 2. It is not desirable to exceed a value of 100 for this ratio, especially for technological reasons and, in particular, in order to limit the risks of corrosion of the equipment. Good results are obtained for a ratio X/Co of the order of about 10 to 50.

The process of the invention is carried out in the presence of cobalt. Any source of cobalt capable of reacting with carbon monoxide in the reaction medium to give cobalt carbonyl complexes can be used within the scope of the present invention. Typical suitable sources of cobalt are, for example, finely divided cobalt metal, inorganic salts, such as cobalt carbonate, and organic salts, in particular, fatty acid salts. Cobalt carbonyls, cobalt hydrocarbonyls or their complexes can also be employed. Among the cobalt derivatives suitable for carrying out the process according to the invention, cobalt acetate and formate, cobalt halides, in particular, cobalt iodide, and dicobalt octacarbonyl may be mentioned.

The reaction is carried out with an effective amount of cobalt. In general, this amount is between about 0.1 and 100, and, preferably, between about 0.5 and 50 milligram atoms, of cobalt per liter of reaction medium.

The process according to the invention also requires the presence of ruthenium. The precise form in which the ruthenium is employed in the reaction is not of fundamental importance within the scope of the present invention. Ruthenium metal in a finely divided form, or ruthenium compounds, such as $RuCl_3$, $RuI_3$, $RuO_2$, $Ru_3(CO)_{12}$ and $Ru(C_5H_7O_2)_3$, can be used.

The amount of ruthenium to be used within the scope of the present process should be at least about 2 gram atoms of ruthenium per gram atom of cobalt employed in the reaction. Preferably, the ratio of the ruthenium to the cobalt is greater than or equal to about 5. No advantage is gained by exceeding a value of about 20 for this ratio.

The carbonylation process of the present invention is preferably, but not necessarily, carried out in the liquid phase. As the reaction is most frequently carried out with the methanol in excess, the simultaneous use of an additional solvent is generally superfluous, but, in principle, it is possible to use such solvents, for example, hydrocarbons, esters, ether, and the reaction products.

Within the scope of the present process, it is not necessary to purify or dry the methanol beforehand. Technical grade methanol can be used.

In accordance with the present process, a mixture of carbon monoxide and hydrogen is reacted with the methanol. It is essential for the said mixture to contain at least about 25 mol percent of hydrogen. In general, mixtures containing up to about 95 mol percent of hydrogen can be used. Mixtures containing from about 40 to 80 mol percent of hydrogen are preferably used. The mixture of gases can contain impurities, such as, for example, carbon dioxide, oxygen, methane and nitrogen.

The reaction is carried out under a total pressure which is generally between about 50 and 400 bars. Preferably, this pressure is between about 100 and 350 bars.

The reaction temperature is at least about 180° C. and can reach about 240° C., if the reaction is carried out without a solvent. In the case where a solvent is used, and this remains optional within the scope of the present invention, the temperature can reach about 300° C. Preferably, the reaction is carried out in a temperature range of about 200° to 240° C.

Specific Description of the Invention

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified. As used in the examples, the term "potential" ethanol is understood to mean the total amount of ethanol which is free or blocked in the form of ethers and esters.

EXAMPLE 1

95 ml. of methanol, 5 ml. of water, 521 mg. (3.67 millimols) of methyl iodide, 1.8 g. (12 millimols) of sodium iodide, 0.127 mg. atom of cobalt in the form of dicobalt octacarbonyl, and 0.657 mg. atom of ruthenium in the form of triruthenium dodecacarbonyl were introduced into a Z8-CNDT 17-12 (AFNOR Standard Specification) stainless steel autoclave having a capacity of 250 ml. After closing the autoclave, a pressure of 140 bars was established using an equimolecular mixture of CO and $H_2$. Shaking by means of a reciprocating system was then started, and the autoclave was heated to 215° C. in the course of about 25 minutes. The pressure in the autoclave then reached 210 bars, and it was kept between 220 and 260 bars by periodically introducing further amounts of a ½ mol ratio mixture of CO and $H_2$. After a reaction time of 1 hours, 15 minutes, at the temperature indicated, the heating and the shaking were stopped; the autoclave was cooled and degassed. The reaction mixture was diluted and analyzed by gas chromatography. It contained 15.2 g. of ethanol, 4.48 g. of methyl ethyl ether, and 0.88 g. of diethyl ether.

The productivity, expressed relative to the potential ethanol, was 160 g. per hour (g/h) and per liter and 2,100 g. per hour and per gram of cobalt.

The experiments below do not fall within the scope of the present invention and are only given by way of comparison.

Control Experiment "A"

Example 1, above, was repeated in the absence of triruthenium dodecacarbonyl; no ethanol was obtained.

Control Experiment "B"

Example 1, above, was repeated in the absence of dicobalt octacarbonyl (the pressure being kept between 220 and 260 bars by periodically introducing further amounts of an equimolecular mixture of CO and $H_2$). After a reaction time of 1 hour, 30 minutes, 1.63 g. of ethanol and 0.83 g. of methyl ethyl ether had been obtained.

Control Experiment "C"

Example 1, above, was repeated, only 0.117 mg. atom of ruthenium in the form of triruthenium dodecacarbonyl being introduced. 6 g. of ethanol and 2.15 g. of methyl ethyl ether were obtained. The productivity in respect of potential ethanol was only 55 g/h and per liter.

EXAMPLE 2

Following the procedure described above in Example 1, 0.118 mg. atom of cobalt in the form of dicobalt octacarbonyl, 0.94 mg. atom of ruthenium in the form of triruthenium dodecacarbonyl, 12 millimols of potassium iodide, 4.67 millimols of methyl iodide, and 100 ml. of methanol were introduced into the autoclave. The temperature was 205° C., and the pressure in the autoclave was kept between 220 and 250 bars by periodically introducing further amounts of a $\frac{2}{3}$ mol ratio mixture of CO and $H_2$. After a reaction time of 1 hour, 15.1 g. of ethanol and 7.33 g. of methyl ethyl ether had been obtained. The productivity in respect of potential ethanol was 210 g. per hour per liter and 3,000 g. per hour per gram of cobalt.

EXAMPLE 3

Following the procedure described above in Example 1, 3 millimols of sodium iodide, 6.8 mols of methyl iodide, 95 ml. of methanol, 5 ml. of water, 2.64 mg. atom of ruthenium in the form of triruthenium dodecacarbonyl, and 0.48 mg. atom of cobalt in the form of dicobalt octacarbonyl were introduced into the autoclave. The reaction temperature was 215° C., and the pressure in the autoclave was kept between 145 and 155 bars by periodically introducing further amounts of a $\frac{1}{2}$ mol ratio mixture of CO and $H_2$. After a reaction time of 30 minutes, 4.15 g. of ethanol and 2.9 g. of methyl ethyl ether had been obtained. Productivity was 130 g/h and per liter and 450 g/h per gram of cobalt.

EXAMPLE 4

Following the procedure described above in Example 1, 100 ml. of methanol, 0.128 mg. atom of cobalt in the form of cobalt iodide, 1.66 mg. atom of ruthenium in the form of ruthenium iodide, and 12 millimols of potassium iodide were introduced into the autoclave. The reaction temperature was 205° C., and the pressure in the autoclave was kept between 180 and 250 bars by periodically introducing further amounts of an equimolecular mixture of CO and $H_2$. After a reaction time of 40 minutes, 11.2 g. of ethanol and 7.7 g. of methyl ethyl ether had been obtained. The productivity in respect of potential ethanol was 270 g/h and per liter and 3,600 g/h and per gram of cobalt.

EXAMPLE 5

Following the procedure described above in Example 1, 3.58 milli-mols of methyl iodide, 90 ml. of methanol, 10 ml. of water, 12 millimols of sodium bromide, 0.66 mg. atom of ruthenium in the form of triruthenium dodecacarbonyl and 0.132 mg. atom of cobalt in the form of dicobalt octacarbonyl were introduced into the autoclave. The reaction temperature was 215° C., and the pressure in the autoclave was kept between 230 and 250 bars by periodically introducing further amounts of a $\frac{1}{2}$ mol ratio mixture of CO and $H_2$. After a reaction time of 40 minutes, 5.24 g. of ethanol and 1.9 g. of methyl ethyl ether had been obtained. The productivity in respect of potential ethanol was 100 g/h and per liter and 1,300 g/h and per gram of cobalt.

EXAMPLE 6

Following the procedure described above in Example 1, 12 milli-mols of lithium iodide, 3.85 milli-mols of butyl bromide, 0.117 mg. atom of cobalt in the form of dicobalt octacarbonyl, 0.66 mg. atom of ruthenium in the form of triruthenium dodecacarbonyl, 90 ml. of methanol, and 10 ml. of water were introduced into the autoclave. The reaction temperature was 225° C., and the pressure in the autoclave was kept between 200 and 235 bars by periodically introducing further amounts of a $\frac{1}{2}$ mol ratio mixture of CO and $H_2$. After a reaction time of 40 minutes, 10.4 g. of ethanol and 0.5 g. of methyl ethyl ether had been obtained. The productivity in respect of potential ethanol was 170 g/h and per liter and 2,500 g/h and per gram of cobalt.

EXAMPLE 7

Following the procedure described above in Example 1, 95 ml. of methanol, 5 ml. of water, 0.126 mg. atom of cobalt in the form of dicobalt octacarbonyl, 0.66 mg. atom of ruthenium in the form of triruthenium dodecacarbonyl, 1.5 milli-mols of sodium iodide and 3.46 milli-mols of methyl iodide were introduced into the autoclave. The reaction temperature was 215° C., and the pressure in the autoclave was kept between 220 and 260 bars by periodically introducing further amounts of a one half mol ratio mixture of CO and $H_2$. After a reaction time of 30 minutes, 11.7 g. of ethanol and 5.45 g. of methyl ethyl ether had been obtained. The productivity in respect of potential ethanol was 330 g/h and per liter and 4,400 g/h and per gram of cobalt.

EXAMPLE 8

Following the procedure described above in Example 1, 12 milli-mols of tetraethylammonium iodide, 3.57 milli-mols of methyl iodide, 0.126 mg. atom of cobalt in the form of dicobalt octacarbonyl, 0.66 mg. atom of ruthenium in the form of triruthenium dodecacarbonyl, 90 ml. of methanol, and 10 ml. of water were introduced into the autoclave. The temperature was 220° C., and the pressure in the autoclave was kept between 210 and 260 bars by periodically introducing further amounts of a $\frac{1}{2}$ mol ratio mixture of CO and $H_2$. After a reaction time of 40 minutes, 11.5 g. of ethanol and 3.40 g. of methyl ethyl ether had been obtained. The productivity in respect of potential ethanol was 220 g/h and per liter and 3,000 g/h and per gram of cobalt.

EXAMPLE 9

Using the procedure described above in Example 1, 1.3 mg. atom of ruthenium in the form of triruthenium dodecacarbonyl, 0.12 mg. atom of cobalt in the form of dicobalt octacarbonyl, 90 ml. of methanol, 10 ml. of water, 3.64 milli-mols of methyl iodide and 6 milli-mols of sodium iodide were introduced into the autoclave. After closing the autoclave, a pressure of 140 bars was established using a $\frac{1}{2}$ mol ratio mixture of CO and $H_2$. The shaker was started up and the autoclave was then heated to 215° C. The pressure in the autoclave then reached 220 bars, and it was kept between 220 and 260 bars by periodically introducing further amounts of this mixture of CO and $H_2$. Under these conditions and after a reaction time of 1 hour, 15 minutes, 14.1 g. of ethanol and 4.8 g. of methyl ethyl ether had been obtained. The productivity in respect of potential ethanol was 150 g/h and per liter and 2,100 g/h and per gram of cobalt.

EXAMPLE 10

Example 7 was repeated, with twice the amount of sodium iodide being introduced. All other conditions being equal, 13.2 g. of ethanol and 5.10 g. of methyl ethyl ether were obtained. The productivity in respect of potential ethanol was 350 g/h and per liter and 4,700 g/h and per gram of cobalt.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process of hydrocarbonylating methanol to produce ethanol, which comprises reacting methanol with a mixture of carbon monoxide and hydrogen, at a temperature of at least about 180° C., under a total pressure of between about 50 and 400 bars, in the presence of cobalt and ruthenium, of at least one ionic halide, the cation of which is chosen from the group consisting of alkali-metal cations, alkaline earth metal cations, quaternary ammonium cations, and quaternary phosphonium cations, and of at least one alkyl halide, the molar ratio $X^-/Co$, $X^-$ being the halide ion originating from the ionic halide, being at least about 5, the molar ratio X/Co, X being the halogen originating from the alkyl halide, being at least about 2, and the gram atom ratio of ruthenium to cobalt being at least about 2.

2. A process according to claim 1, wherein the alkyl halide is selected from the among the class consisting of chlorides, bromides, and iodides, having from about 1 to 4 carbon atoms in the molecule.

3. A process according to claim 2, wherein the alkyl halide is a methyl halide.

4. A process according to claim 3, wherein the methyl halide is at least partially produced in situ from at least one compound chosen from the group consisting of molecular chlorine, molecular bromine, and molecular iodine, the corresponding hydrohalic acids, cobalt bromide, and iodide and ruthenium bromide and iodide.

5. A process according to claim 1, wherein the cation of the ionic halide is chosen from among alkali metal cations and alkaline earth metal cations.

6. A process according to claim 1, wherein the ionic halide is an iodide.

7. A process according to claim 1, wherein the alkyl halide is an iodide.

8. A process according to claim 1, wherein the ratio $X^-/Co$ is between about 10 and 100.

9. A process according to claim 1, wherein the ratio $X^-/CO$ is between about 10 and 50.

10. A process according to claim 1, wherein the concentration of the cobalt is between about 0.1 and 100 milligram atoms per liter of reaction medium.

11. A process according to claim 1, wherein the concentration of the cobalt is between about 0.5 and 50 milligram atoms per liter of reaction medium.

12. A process according to claim 1, wherein the gram atom ratio Ru/Co is between about 5 and 20.

13. A process according to claim 1, wherein the total pressure is between about 100 and 350 bars.

14. A process according to claim 1, wherein the temperature is between about 200° and 240° C.

15. A process according to claim 1, wherein said process is conducted in the liquid phase.

16. A process according to claim 1, wherein the mixture of carbon monoxide and hydrogen contains at least about 25 mol percent of hydrogen.

17. A process according to claim 1, wherein the mixture of carbon monoxide and hydrogen contains between about 25 and 95 mol percent of hydrogen.

18. A process according to claim 1, wherein the mixture of carbon monoxide and hydrogen contains from about 40 to 80 mol percent hydrogen.

* * * * *

UNITED STATES PATENT AND TRADEMARK OFFICE
CERTIFICATE OF CORRECTION

PATENT NO. : 4,324,927

DATED : April 13, 1982

INVENTOR(S) : Gauthier-Lafaye et al.

It is certified that error appears in the above—identified patent and that said Letters Patent is hereby corrected as shown below:

Col. 7, line 20 - "mols" should be --millimols--.

Signed and Sealed this

Tenth Day of August 1982

[SEAL]

Attest:

GERALD J. MOSSINGHOFF

*Attesting Officer*     *Commissioner of Patents and Trademarks*